United States Patent [19]

Faure et al.

[11] 4,447,631

[45] May 8, 1984

[54] REDISTRIBUTION OF TETRAMETHYLSILANE/DIMETHYLDICHLOROSILANE INTO TRIMETHYLCHLOROSILANE

[75] Inventors: Alphonse Faure, Vienne; Robert Magne, Roussillon, both of France

[73] Assignee: Rhone-Poulenc Industries, Paris, France

[21] Appl. No.: 148,587

[22] Filed: May 12, 1980
(Under 37 CFR 1.47)

[30] Foreign Application Priority Data

May 10, 1979 [FR] France ............................... 79 11837

[51] Int. Cl.$^3$ ............................................. C07F 7/12
[52] U.S. Cl. ................................................... 556/469
[58] Field of Search ......................................... 556/469

[56] References Cited

U.S. PATENT DOCUMENTS

| | | | |
|---|---|---|---|
| 3,728,368 | 4/1973 | Bazouin et al. | 556/469 |
| 3,793,357 | 2/1974 | McEntee | 556/469 |
| 4,266,068 | 5/1981 | Allain et al. | 556/469 X |

OTHER PUBLICATIONS

Rathousky, J. et al., Coll. Czechoslov. Chem. Com. 25, pp. 1807–1813, 1960.

*Primary Examiner*—Paul F. Shaver
*Attorney, Agent, or Firm*—Burns, Doane, Swecker & Mathis

[57] ABSTRACT

Tetramethylsilane/dimethyldichlorosilane admixtures are redistributed into trimethylchlorosilane by passing same, in vapor phase, through a reaction zone under mild temperatures and comprising a catalytic amount of anhydrous aluminum chloride granules. Preferably, the redistribution is conducted under atmospheric pressure.

11 Claims, No Drawings

REDISTRIBUTION OF TETRAMETHYLSILANE/DIMETHYLDICHLOROSILANE INTO TRIMETHYLCHLOROSILANE

BACKGROUND OF THE INVENTION

1. Field of the Invention

The present invention relates to an improved process for the preparation of trimethylchlorosilane, and, more especially, to the preparation of trimethylchlorosilane via redistribution between tetramethylsilane and dimethyldichlorosilane, such redistribution reaction being catalyzed by particulate aluminum chloride, advantageously aluminum chloride granules.

2. Description of the Prior Art

Redistribution reactions between tetraalkylsilanes and alkylchlorosilanes, either in the presence of hydrogensilanes, and with the aid, as catalysts, of aluminum chloride or related compounds (alkaline chloroaluminates, complexes between alkyl aluminum dihalides and alkaline halides) are very well known to this art.

Nonetheless, the conditions under which the aforenoted redistributions proceed are quite severe and militate against broad application thereof. Thus, certain of such redistributions require temperatures in excess of 150° C. and pressures higher than 10 bars (compare U.S. Pat. No. 3,135,778), or even temperatures in excess of 250° C., under either atmospheric pressure (French Pat. No. 1,089,575) or pressures in excess of 100 bars (French Pat. No. 1,264,256).

Certain others of such processes may be effected at lower temperatures and at atmospheric pressure. However, when operating under such experimental conditions, the chemical literature reflects that the redistribution must take place in the liquid phase (French Pat. No. 1,147,688), which implies the use of large space occupying apparatus having low productivity. These space requirements may be reduced (U.S. Pat. No.3,793,357) by conveying or charging the alkylsilanes to be redistributed, in the vapor state, into a reaction medium comprising solid aluminum chloride and liquid arylhalosilanes having boiling points higher than those of the alkylsilanes, but here too disadvantages may arise; in particular, serious risk of redistribution between the alkylsilanes and the alkylhalosilanes exists. Furthermore, it is always difficult to separate the aluminum chloride from the silanes wherein it is dispersed or dissolved.

SUMMARY OF THE INVENTION

Accordingly, a major object of the present is the provision of an improved tetramethylsilane/dimethyldichlorosilane redistribution for the preparation of trimethylchlorosilane, which redistribution is far more simple and efficient than those which have to date characterized this art, and which can be conducted under mild conditions, e.g., at low temperatures not exceeding 120° C. and at atmospheric pressure.

Briefly, the present invention features a process for the preparation of trimethylchlorosilane by means of a redistribution reaction between tetramethylsilane and dimethyldichlorosilane utilizing anhydrous aluminum chloride as the catalyst, and characterized in that the two reactants are conveyed in vapor state through a reaction zone maintained at a temperature of from about 75° C. to 120° C., said reaction zone containing a catalytically effective amount of particulate, or granular aluminum chloride.

DETAILED DESCRIPTION OF THE INVENTION

More particularly, the process according to the invention does not require the use of large and expensive apparatus and other technical means. It is sufficient to utilize therefor a simple, preferably tubular reactor, to merely change such reactor with a catalytic amount of the anhydrous aluminum chloride granules (of arbitrary grain size), to heat the charged reactor to a temperature from 75° to 120° C., preferably 80° to 110° C., and thence to simply pass therethrough by introduction at either end thereof, a gaseous mixture comprising the vapors of tetramethylsilane and dimethyldichlorosilane. The trimethylchlorosilane formed in this manner and the unreacted tetramethylsilane and dimethyldichlorosilane are recovered from the other end of the reactor; the trimethylchlorosilane may be isolated and recovered by means of distillation while the unreacted silanes may be recycled into the reactor.

As mentioned hereinabove, the granules of aluminum chloride may be of any size; it is merely necessary that same can readily and conveniently be introduced or charged into the reactor. However, it is of advantage to utilize the commercially available granules, typically those ranging in diameter from 0.1 to 10 mm, preferably from 0.3 to 6 mm.

The redistribution reaction can be represented by the sequence:

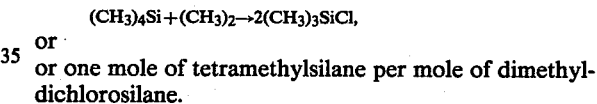

or one mole of tetramethylsilane per mole of dimethyldichlorosilane.

The reaction may also be conducted with mixtures that do not necessarily contain equimolar amounts of the two reactants.

Thus, the molar ratio of the tetramethylsilane to the dimethyldichlorosilane may vary over a rather broad range, from 0.2 to 1.8, preferably 0.4 to 1.4.

The duration of the contact time between the two reactants within the reactor, which depends upon the ratio of the reaction volume of the reactor to the flow rate of the reactants, may vary from a few seconds to several hundred seconds, for example, from 3 seconds to 300 seconds, preferably from 6 seconds to 150 seconds.

It is advantageous to utilize as co-catalysts, or accelerators for the redistribution reaction, hydrogenochlorosilanes having the general formula: $(CH_3)_a HSiCl_{3-a}$, wherein the symbol a represents zero, 1 or 2. Such hyrogenochlorosilanes, selected from the group consisting of $HSiCl_3$, $(CH_3)HSiCl_2$ and $(CH_3)_2HSiCl$, comprise from 0.1 to 15% by weight, preferably from 0.5 to 10% by weight, of the combined weight of the tetramethylsilane and dimethyldichlorosilane.

These co-catalysts, by accelerating the redistribution reaction, enable the use of higher flow rates for the reactants (thus decreasing contact times) and serve to improve the rate of conversion of said two reactants.

Additionally, and contrary to that which reasonably could be expected, conveying a gaseous mixture of tetramethylsilane and dimethyldichlorosilane, and optionally the hydrogenochlorosilanes having the formula $(CH_3)_a HSiCl_{3-a}$, over aluminum chloride heated to 75°–120° C., does not result in entrainment of any vapors of particles of aluminum chloride.

The redistribution reaction, thus, may either be discontinuous or continuous. It occasionally transpires that the catalyst loses minor activity due to the deposition thereon of impurities and/or unsaturated hydrocarbons possibly present in the reactant mixtures. It is then sufficient to sweep the reactors, at their operating temperature of 75° to 120° C., with gaseous hydrochloric acid for varying periods of time, from twenty minutes to several hours, to restore or regenerate the catalytic activity of the aluminum chloride.

The redistribution reaction is most preferably effected at atmospheric pressure; it may be effected at pressures either lower or higher than atmospheric without gaining any advantage that would compensate for the technical problems which would arise upon use of pressures other than atmospheric.

The process according to the invention also makes it possible to utilize that tetramethylsilane as a reactant which is a byproduct of the direct synthesis of chlorosilanes, effected by passing methyl chloride over a Si-Cu contact mass heated to 300° C. Such synthesis results in the preparation of methylchlorosilanes, such as those of the formulae $CH_3SiCl_3$, $(CH_3)_2SiCl_2$, $(CH_3)_3SiCl$, $CH_3HSiCL_2$ and also to complex mixtures of other silicon compounds. In particular, the mixtures exiting the top of the distillation column and comprising the products of such direct synthesis include tetramethylsilane (in large percentages), halogenohydrogenosilanes such as those of the formulae $HSiCl_3$, $(CH_3)_2HSiCl$, and not infrequently unsaturated hydrocarbons.

The tetramethylsilane thus prepared may be used in pure state, after treatment of the first fraction of the distillates, or in the form of the above-mentioned mixtures.

Insofar as the dimethyldichlorosilane is concerned, which is produced in very large quantities by the several silicone manufacturers, same is preferably employed in essentially pure state; but mixtures containing a high percentage thereof may also be used, for example, mixtures comprising, in addition to the dimethyldichlorosilane, minor amounts of silanes of the formulae $(CH_3)_3SiCl$ and $CH_3HSiCl_2$.

The trimethylchlorosilane prepared according to the process of the invention is widely used in the manufacture of rubbers, oils and organosilicon resins. Because trimethylchlorosilane is produced only in small percentages in the course of any direct synthesis, it is profitable to manufacture same on an industrial scale in supplementary amounts from byproducts such as tetramethylsilane, as aforesaid.

In order to further illustrate the present invention and the advantages thereof, the following specific examples are given, it being understood that same are intended only as illustrative and in nowise limitative.

EXAMPLE 1

Apparatus comprising the following was employed:

[1] An 80 cm long vertical column, having an internal diameter of 1.7 cm, a useful volume of 182 cm$^3$, and equipped with a double jacket to heat the column by means of the circulation therein of a heat transfer liquid, i.e., a polymethylphenylsiloxane oil having a viscosity of 550 mPa.s at 25° C.; the column was packed with 210 g of anhydrous aluminum chloride granules, having an average particle diameter of 4.2 mm;

[2] A system for the introduction of the reactants into [1] comprising a pouring vessel (containing a liquid mixture of silanes) and an evaporator heated to 140°–150° C., said evaporator being attached to the base of the column; the liquid mixture of silanes descends by gravity into the evaporator by means of a tube connecting the bottom of the vessel to the evaporator;

[3] A device for the condensation of the vapors, branched onto the outlet of the column, comprising a cooler (cooled by water at a temperature on the order of 18° C.), communicating with a graduated receiving vessel; a gas outlet is provided on the body of the cooler for the circulation of noncondensable vapors, the outlet being connected to a Dewar vessel cooled to −80° C.

The column and its packing were heated to 90° C. by the circulation, in the double jacket, of the heat transfer fluid heated to this temperature, and a regular flow of the liquid mixture of silanes, consisting of silanes of the formulae $(CH_3)_4Si$, $(CH_3)_2SiCl_2$, $HSiCl_3$ amd $(CH_3)_2HSiCl$, in the molar ratios of 1/1/0.007/0.07, respectively, and traces of unsaturated hydrocarbons, was established into the evaporator. The amount of the silanes $HSiCl_3$ and $(CH_3)_2HSiCl$ was 3.5% by weight of the combined weight of the silanes $(CH_3)_4Si$ and $(CH_3)_2SiCl_2$.

The mean flow of the mixture of silanes was approximately 55 cm$^3$/h, which determined, as a function of the temperature applied and the reaction volume of the column, the contact time of the vapor mixture in the column, i.e., 26 seconds.

In this experiment, which was for a duration of 6 hours, 30 minutes, there were utilized 314.6 g of the silane mixture comprising 1.4 mole of $(CH_3)_4Si$ and 1.4 mole of $(CH_3)_2SiCl_2$ and there were recovered in the receiving and the Dewar vessel, 307 g of a mixture comprising 0.55 mole of $(CH_3)_4Si$, 0.56 mole of $(CH_3)_2SiCl_2$ and 1.65 mole of $(CH_3)_3SiCl$. The degree of conversion of $(CH_3)_4Si$ or of $(CH_3)_2SiCl_2$ was thus approximately 60%, and essentially all of the converted $(CH_3)_3SiCl$ and $(CH_3)_2SiCl_2$ was selectively redistributed into $(CH_3)_3SiCl$. Therefore, selectivity relative to the formation of $(CH_3)_3SiCl$ was on the order of 99%.

EXAMPLE 2

The procedure of Example 1 was repeated utilizing the same mixture of silanes, except that the flow rate of the mixture was 46 cm$^3$/h in place of 55 cm$^3$/h, which gave rise to a contact time of 31 seconds instead of 26 seconds.

Furthermore, the duration of redistribution was 190 hours.

A degree of conversion of $(CH_3)_4Si$ and of $(CH_3)_2SiCl_2$ of 56% and of selectivity relative to the formation of $(CH_3)_3SiCl$ of 95% were obtained.

EXAMPLE 3

Following the termination of the experiment described in Example 2, a regenerating flow of gaseous hydrochloric acid was established for 2 hours, at a rate of 1 mole/h into the column, heated at 90° C. The passing of the hydrochloric gas through the granules of aluminum chloride was then replaced by a flow of dry nitrogen for 8 minutes. An equimolar mixture of $(CH_3)_4Si$ and $(CH_3)_2SiCl_2$ was then passed into the column, heated to 90° C., at a rate of 50 cm$^3$/h for three hous, the contact time of the silane vapors in the column being 28 seconds.

A degree of conversion of $(CH_3)_4Si$ and of $(CH_3)_2SiCl_2$ of 54% and a selectivity relative to the formation of $(CH_3)_3SiCl$ of 95%, were noted.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. A process for the redistribution of a tetramethylsilane and dimethyldichlorosilane admixture into trimethylchlorosilane, comprising contacting such admixture, in vapor phase, with a catalytically effective amount of a catalyst selected from the group consisting of granular anhydrous aluminum chloride and mixtures thereof with a hydrogen-chlorosilane having the formula $(CH_3)_aHSiCl_{3-a}$, where a is 0, 1 or 2, at a temperature ranging from about 75° C. to 120° C.

2. The process as defined by claim 1, said redistribution being effected at atmospheric pressure.

3. The process as defined by claims 1 or 2, the hydrogenosilane being present in an amount of from about 0.1 to 15% of the total weight of the tetramethylsilane and dimethyldichlorosilane.

4. The process as defined by claims 1 or 2, the molar ratio of the tetramethylsilane to the dimethyldichlorosilane in the admixture ranging from 0.2 to 1.8.

5. The process as defined by claim 4, said molar ratio ranging from 0.4 to 1.4

6. The process as defined by claims 1 or 2, essentially equimolar amounts of tetramethylsilane and dimethyldichlorosilane comprising the admixture.

7. The process as defined by claims 1 or 2, the aluminum chloride granules ranging from 0.1 to 10 mm in diameter size.

8. The process as defined by claims 1 or 2, the contact time for the redistribution ranging from 3 seconds to 300 seconds.

9. The process as defined by claims 1 or 2, such admixture further comprising a minor amount of a member selected from the group consisting of $CH_3SiCl_3$, $(CH_3)_3SiCl$, $CH_3HSiCl_2$, halohydrogenosilane, unsaturated hydrocarbon, and mixtures thereof.

10. The process as defined by claims 1 or 2, the redistribution being conducted in a tubular reaction zone.

11. The process as defined by claims 1 or 2, wherein the granular aluminum chloride is pre-treated with aqueous hydrochloric acid at a temperature of from about 75° C. to 120° C.

* * * * *